(12) United States Patent
Sansoucy

(10) Patent No.: US 7,329,234 B2
(45) Date of Patent: Feb. 12, 2008

(54) SELF-OCCLUDING CATHETER

(75) Inventor: Michael R. Sansoucy, Franklin, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1328 days.

(21) Appl. No.: 09/764,659

(22) Filed: Jan. 17, 2001

(65) Prior Publication Data

US 2001/0041857 A1 Nov. 15, 2001

Related U.S. Application Data

(63) Continuation of application No. 09/368,611, filed on Aug. 5, 1999, now Pat. No. 6,179,806.

(51) Int. Cl.
*A61M 1/00* (2006.01)

(52) U.S. Cl. .......... 604/33; 604/247; 137/862; 137/871

(58) Field of Classification Search .......... 604/27, 604/30, 33, 35, 65, 236, 246, 247, 254; 137/84, 137/861, 862, 871
See application file for complete search history.

(56) References Cited

U.S. PATENT DOCUMENTS

| | | | |
|---|---|---|---|
| 4,036,210 A | * | 7/1977 | Campbell et al. .......... 604/26 |
| 4,668,215 A | | 5/1987 | Allgood |
| 5,034,000 A | | 7/1991 | Freitas et al. |
| 5,197,951 A | | 3/1993 | Mahurkar |
| 5,205,819 A | * | 4/1993 | Ross et al. .......... 128/DIG. 12 |
| 5,399,172 A | * | 3/1995 | Martin et al. .......... 604/248 |
| 5,478,318 A | * | 12/1995 | Yoon .......... 604/167.05 |
| 5,486,159 A | | 1/1996 | Mahurkar |
| 5,549,651 A | * | 8/1996 | Lynn .......... 251/334 |
| 5,676,657 A | * | 10/1997 | Yoon .......... 604/167.03 |
| 6,162,201 A | * | 12/2000 | Cohen et al. .......... 604/101.01 |
| RE37,357 E | * | 9/2001 | Lynn .......... 251/334 |

FOREIGN PATENT DOCUMENTS

WO     WO 94/02195     * 2/1994

* cited by examiner

*Primary Examiner*—Brian L. Casler
*Assistant Examiner*—Jeremy Thissell
(74) *Attorney, Agent, or Firm*—Fay Kaplun & Marcin, LLP

(57) ABSTRACT

A self-occluding catheter includes a body portion for connection to extracorporeal equipment. An elongated tubular extension is provided for insertion into a body cavity. The body portion includes a resiliently biased spool supported therein which is slidable between an open and a closed position for alternately permitting and stopping the flow of blood through the catheter during a given medical procedure. The biasing device for resilient biasing the spool preferably comprises one or more magnets fixed within the body portion which generate a magnetic force for urging the magnetically polarized spool to its closed position.

10 Claims, 6 Drawing Sheets

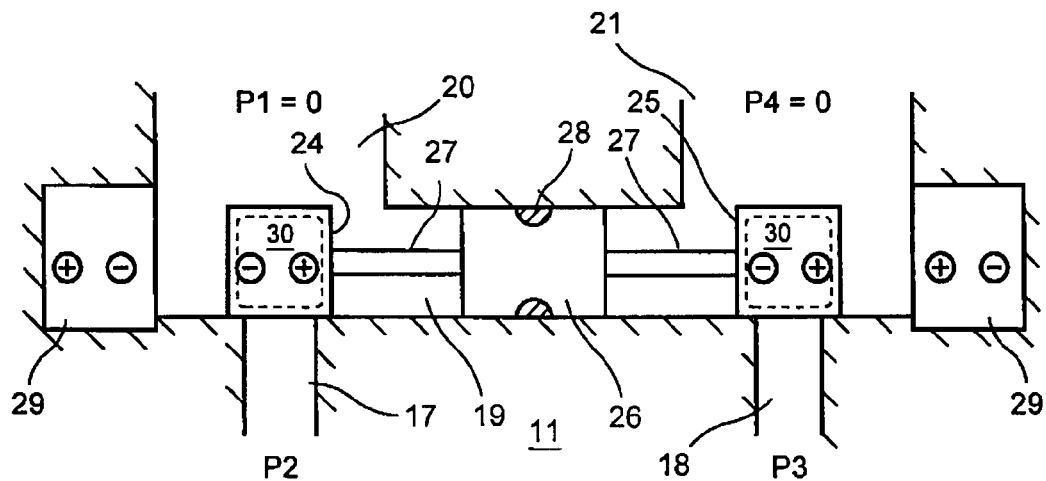
F I G. 2a
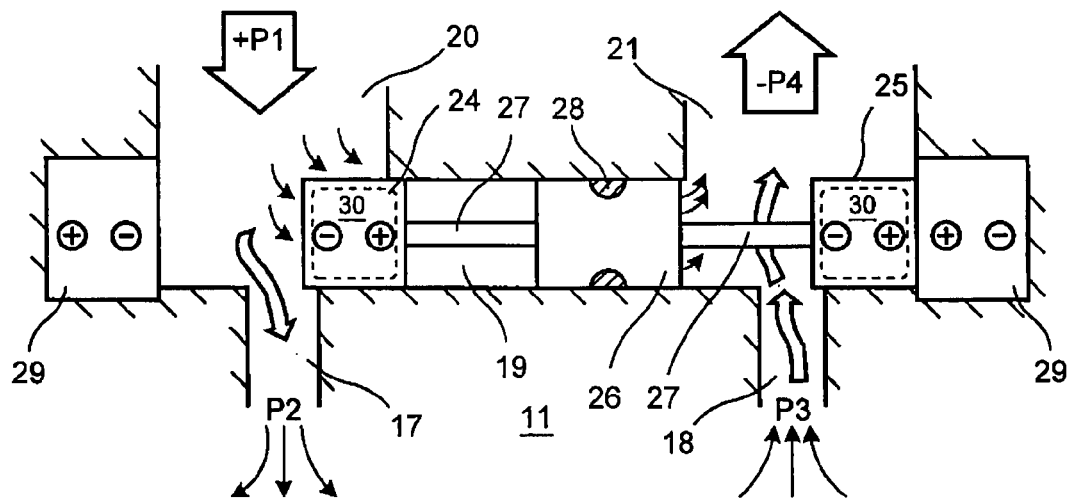
F I G. 2b
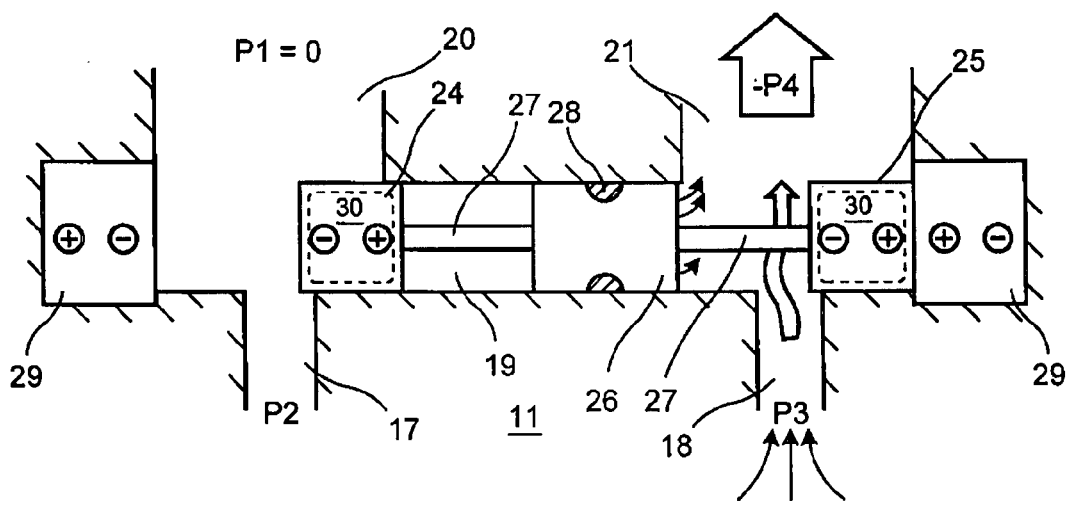
F I G. 2c

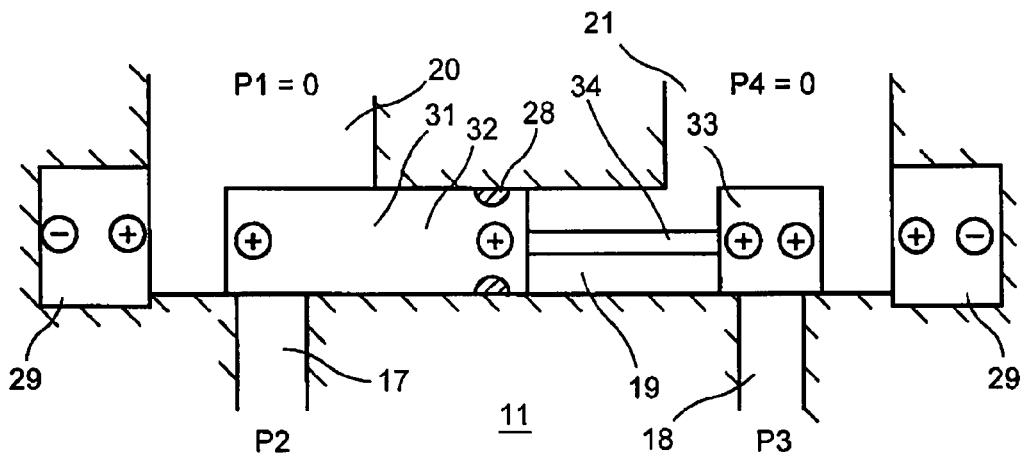
F I G. 4a
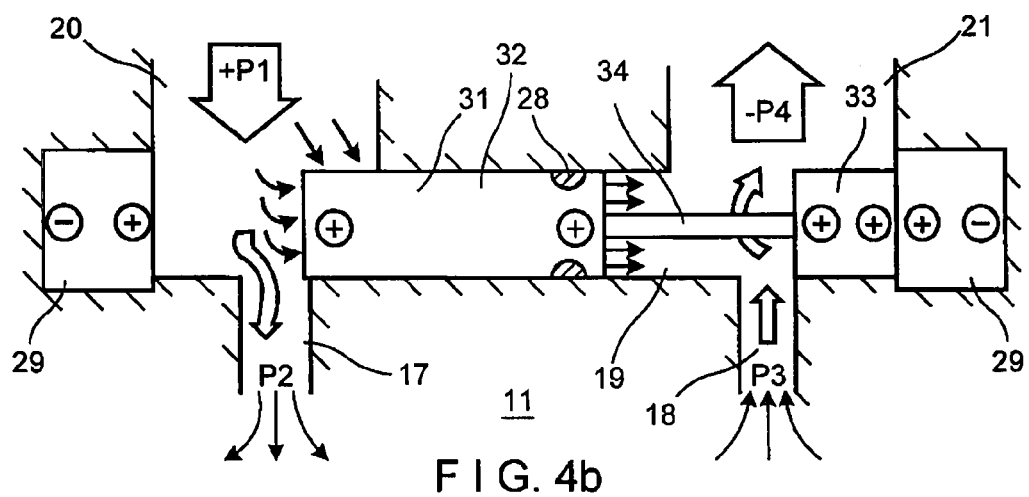
F I G. 4b
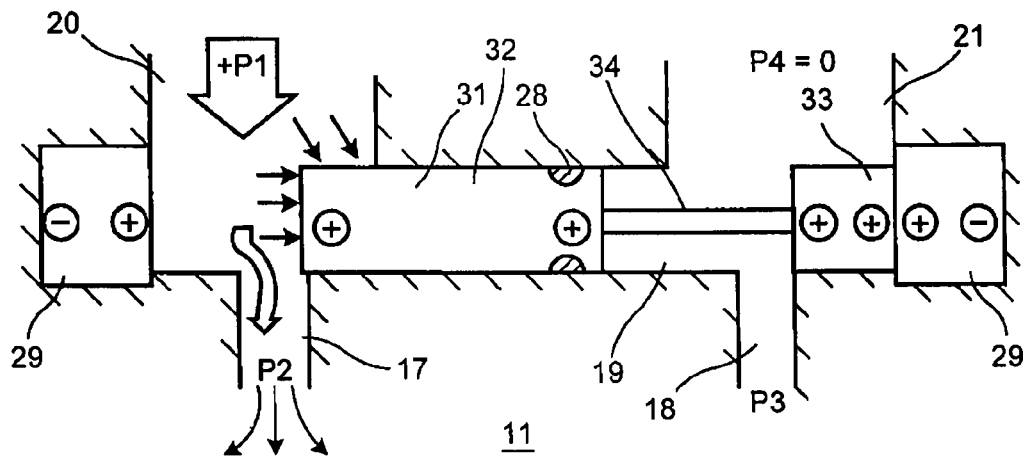
F I G. 4c

SELF-OCCLUDING CATHETER

This application is a continuation of U.S. application Ser. No. 09/368,611, filed on Aug. 5, 1999 now U.S. Pat. No. 6,179,806.

BACKGROUND OF THE INVENTION

1. Field of the Invention

The present invention relates generally to catheters for use in medical applications such as hemodialysis wherein fluids are withdrawn and/or introduced into a cavity of the body. The invention relates particularly to a hemodialysis catheter having internal means to automatically stop blood flow after a dialysis procedure has been conducted.

2. Description of the Prior Art

Hemodialysis is a process of mass transfer in which certain chemical substances accumulated in the blood because of kidney failure are transferred from the blood across a semipermeable membrane to a balanced salt solution in a dialysis machine. In a typical hemodialysis procedure, a double-lumen catheter is utilized to simultaneously withdraw blood from a body cavity through one channel or lumen for processing in a dialysis machine and to reintroduce the processed blood back to the patient through a separate lumen.

Such catheters typically include a catheter hub or branch connector for connecting the catheter to tubes leading to and from a dialysis unit. The hub or connector may also be adapted for accommodating injection syringes, or other extracorporeal equipment which may be required for a selected medical procedure. To facilitate connection of the catheter hub to such equipment, the hub typically includes extension tubes which accommodate clamps for opening and closing the fluid passage ways of the respective extension tubes. The clamps serve as on-off valves for controlling the flow of blood between the catheter and dialysis unit or other medical equipment. Typical dialysis catheters are shown in U.S. Pat. No. 5,197,951 and U.S. Pat. No. 5,486,159 both to Mahurkar.

The requirement of extension tubes and clamps to prevent blood flow after a dialysis or other medical procedure has been conducted, makes conventional dialysis catheters somewhat cumbersome and uncomfortable for the patient. Manual operation of the clamps also requires additional manipulation by the dialysis professional to complete the procedure. The external clamps are also prone to tampering and inadvertent opening or loosening.

Accordingly, it would be desirable to provide a small, light-weight catheter which reduces the discomfort to the patient and is also automatic in nature thereby reducing the manipulation required by the dialysis professional to complete the procedure.

SUMMARY OF THE INVENTION

It is an object of the present invention to provide a small, light-weight catheter which is uncumbersome and reduces the discomfort to the patient.

It is another object of the present invention to provide a catheter which is automatic in nature requiring minimum manipulation by a medical professional to complete a given medical procedure.

It is a further object of the present invention to provide a catheter which eliminates the need for extension tubes and clamps which are prone to tampering and/or inadvertent opening or loosening.

In accordance with one form of the present invention, a self-occluding catheter generally includes a body portion for connection to extracorporeal equipment and an elongated tubular portion for insertion into a body cavity. The elongated tubular portion may be fixed to or made removable from the body portion. The tubular portion includes at least one lumen which is in fluid communication with at least one internal fluid conduit of the body portion. The body portion also includes an internal transverse bore which is in fluid communication with the internal fluid conduits of the body portion. Supported within the transverse bore is a spool which is slidable between an open and a closed position. A biasing device is provided adjacent the spool for resiliently urging the spool to a normally closed position wherein the spool blocks the internal fluid conduits thereby preventing fluid flow through the body portion. When a positive or a negative fluid pressure is applied to the equipment connection end of the body portion, the spool slides to an open position thereby permitting fluid flow through the body portion. When the fluid pressure is terminated the biasing device returns the spool to its closed position whereby the internal fluid conduits are again blocked.

The biasing device preferably comprises one or more magnets fixed within the body portion which generate a magnetic force for urging a magnetically polarized spool to its closed position. In the preferred embodiment, one or more magnets are integrally molded within the spool to provide the magnetic charge to the spool. The spool is preferably in the form of a cylindrical member having two opposite end portions, a shoulder portion positioned between the end portions and a reduced diameter neck portion positioned between each of the end portions and the shoulder portion. The shoulder portion slides in close fitting relationship with the transverse bore and is acted upon by the positive or negative fluid pressure applied to the equipment connection end to move the spool to its open position. In the spool's closed position, the end portions block both an inlet and an outlet fluid conduit of the body to prevent fluid flow through the body.

A preferred form of the catheter, as well as other embodiments, objects, features and advantages of this invention will be apparent from the following detailed description of illustrative embodiments thereof which is to be read in conjunction with the accompanying drawings.

BRIEF DESCRIPTION OF THE DRAWINGS

FIGS. 2a, 2b and 2c are schematic drawings illustrating the operation of the catheter shown in FIG. 1.

FIGS. 4a, 4b and 4c are schematic drawings illustrating the operation of the catheter shown in FIG. 3.

DETAILED DESCRIPTION OF THE PREFERRED EMBODIMENTS

Figure 1:
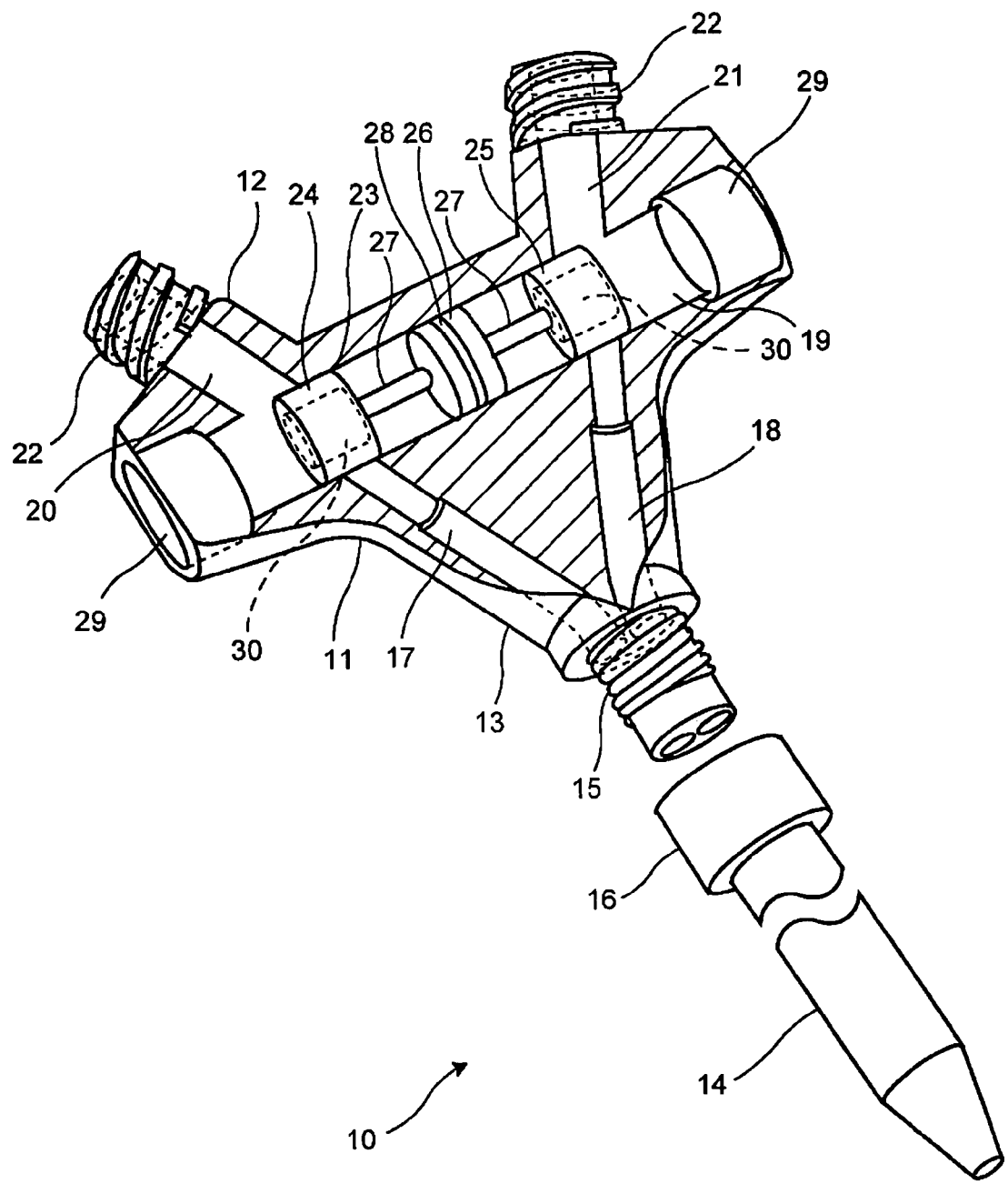
FIG. 1 is a perspective, partial cross-sectional, view of the preferred embodiment of the self-occluding catheter formed in accordance with the present invention.

Referring to FIG. 1, a preferred embodiment of the self-occluding catheter formed in accordance with the present invention is shown. The catheter shown in FIG. 1 is a double-lumen catheter adapted for hemodialysis procedures, however, the present invention may be utilized in single-lumen catheters, as discussed below, or in multiplelumen catheters which may be adapted for any other of a variety of medical procedures.

Figure 3:
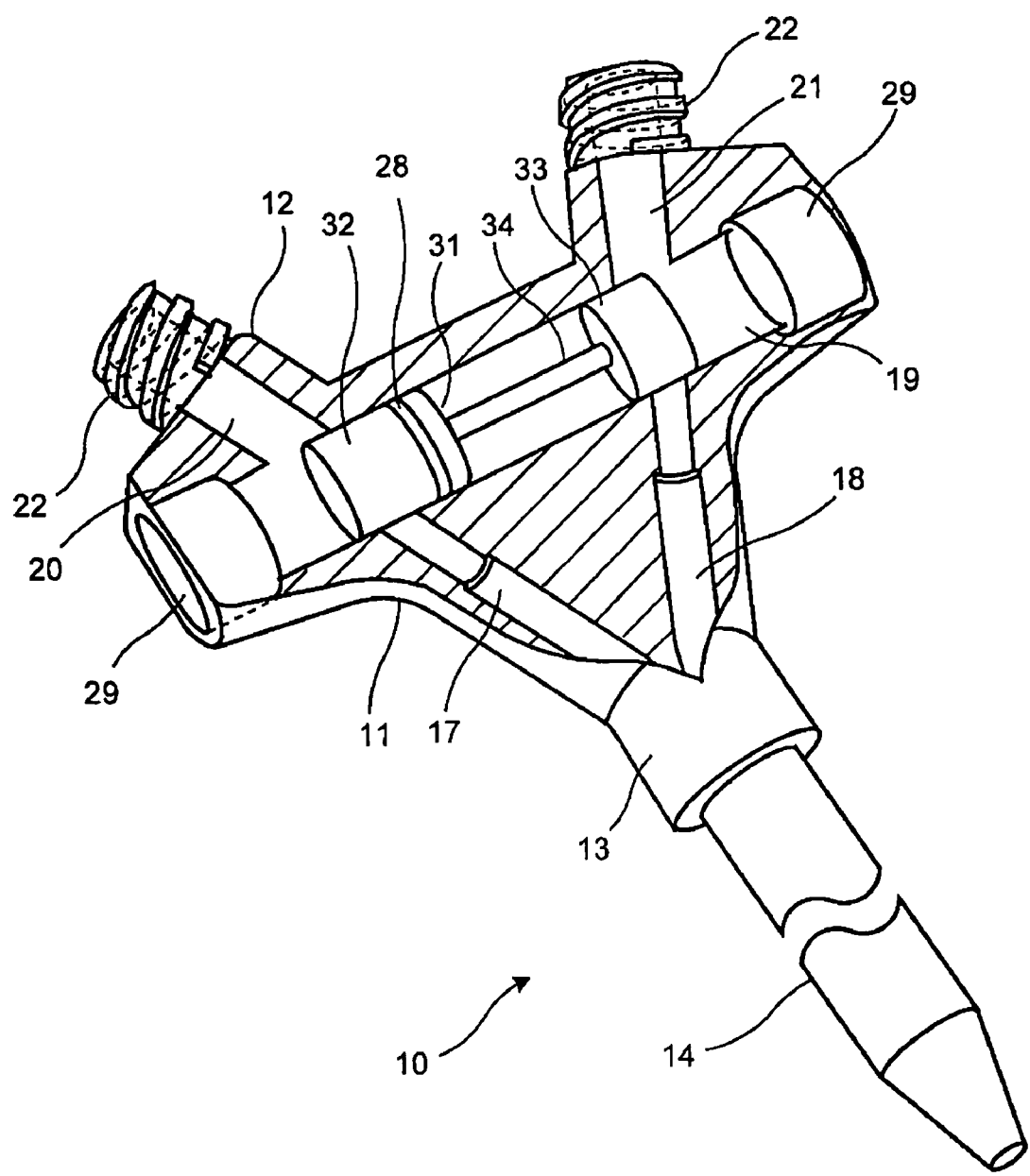
FIG. 3 is a perspective, partial cross-sectional, view of an alternate embodiment of the self-occluding catheter formed in accordance with the present invention.

The preferred form of the self-occluding catheter 10 generally includes a body portion 11, having a generally triangular cross-sectional configuration defining a wide proximal end 12, and a narrow distal end 13. An elongated flexible tubular extension 14 is connected to the distal end 13 of the body portion. As used herein the terms proximal and distal are used to denote opposite ends of body portion 11. The distal end 13 of the body portion is provided with an external thread 15 which engages with a cooperating threaded connector 16 of the tubular extension 14 so that the tubular extension may be removed and replaced with other tubular portions or with other catheters. Thus, the body portion 11 alone may take the form of a catheter connector for connecting conventional catheters to extracorporeal medical equipment. Alternatively, the body portion 11 and the tubular portion 12 may be molded together as a unitary catheter as shown in FIG. 3. In either case, the tubular portion 14 must be flexible to allow for insertion into a body cavity. The body portion 11 and the tubular portion 14 may be molded or extruded of any known biocompatible polymeric material. Silicone is a preferred material for these applications because it is inert and is tolerated by the human body for long periods of time without reaction.

The body portion 11 includes an inlet fluid conduit 17, an outlet fluid conduit 18, a transverse bore 19, an inlet port 20 and an outlet port 21 formed therein to be in fluid communication. The inlet and outlet fluid conduits 17 and 18 extend from the distal end 13 of the body 11 and intersect with the transverse bore 19. The inlet and outlet ports 20 and 21 extend from the proximal end 12 of the body and intersect with the transverse bore 19 adjacent respective inlet and outlet fluid conduits 17 and 18. The inlet and outlet fluid conduit 17 and 18 are also in fluid communication with respective inlet and outlet lumens (not shown) of the tubular extension 14 when the tubular portion is connected to the body 11. The conduits 17 and 18, the bore 19 and the ports 20 and 21 may be formed by conventional machining techniques, e.g. drilling, reaming etc,. or may be internally molded within the body portion. The inlet and outlet ports 20 and 21 are provided with external threads 22 at the proximal end 12 of the body portion 11 which cooperate with threaded connectors supplied on conventional tubing of extracorporeal equipment such as a hemodialysis unit (not shown). The inlet and outlet fluid conduits and ports are formed in the shape of a "V" as shown in FIG. 1, however any spatial configuration may be utilized.

As mentioned above, the transverse bore 19 is in fluid communication with the inlet and outlet fluid conduits 17 and 18 and the inlet and outlet ports 20 and 21. Slidably supported within the transverse bore 19 is a spool 23 which may be formed of a similar biocompatible material as the body 11 and tubular extension 14. In the preferred embodiment, the spool 23 is an elongate member formed with opposite end portions 24 and 25, a central shoulder portion 26 spaced between the end portions and a neck portion 27 positioned between and joining each end portion 24 and 25 and the shoulder portion 26. The spool 23 is generally cylindrical with the shoulder portion 26 having a diameter approximately equal to but slightly less than the diameter of the transverse bore 19 so that the shoulder portion 26 is positioned in close sliding relationship within the transverse bore. The diameter of the end portions 24 and 25 is preferably equal to the diameter of the shoulder portion 26 and the diameter of the neck portion 27 is smaller than the diameters of both the end portions and the shoulder portion. The length of the end portions is such that when the spool 23 is centrally positioned within the transverse bore 19 of the body portion 11 the end portions completely close or occlude the inlet and outlet fluid conduits 17 and 18. The shoulder portion 26 includes a fluid sealing ring 28 to prevent fluid flow therepast and between the inlet and outlet fluid conduits 17 and 18. The fluid sealing ring 28 shown in FIGS. 1-6 comprises an annular groove formed on the shoulder portion 26 which is fitted with an O-ring, however, other seals such as a flaring-pressure seal, a lip seal or a ball bearing seal may be utilized.

The spool 23 is resiliently urged into its central closed position, (in which the inlet and outlet fluid conduits 17 and 18 are occluded), by a biasing device. In the preferred embodiment, the biasing device comprises two external magnets 29, fixed in opposite ends of the transverse bore 19, which generate a magnetic force upon a magnetically charged or polarized spool 23. The spool is magnetically charged by providing internal magnets 30 within end portion 24 and 25. Preferably, internal magnets 30 are integrally molded into the end portions 24 and 25 to provide the magnetic polarization to the spool 23. The polarities of the internal magnets 30 and the external magnets 29 are positioned such that the magnets generate a magnetic force which urges and maintains the spool 23 in a central closed position within the transverse bore 19 between the two opposite external magnets 29.

Having described the self-occluding catheter shown in FIG. 1 its operation may be schematically described with respect to FIGS. 2a, 2b and 2c.

FIG. 2a shows the location of the spool 23 in its normally closed central position wherein the end portions 24 and 25 occlude the inlet and outlet fluid conduits 17 and 18. The normally closed position is maintained by the respective polarities of magnets 29 and 30 as indicated in FIGS. 2a-2c. This is the position of the spool when injection caps (not shown) are in place on the threaded port connectors 22 prior to connecting the catheter 10 to a dialysis unit. In a typical hemodialysis procedure, the tubular extension 14 of the double-lumen catheter 10 is introduced in the direction of blood flow within a large vein in a conventional manner. Once the catheter 10 is in place, the injection caps are removed and the inlet and outlet ports 20 and 21 of the proximal end 12 of the body 11 are connected to conventional tubes of a dialysis unit. Prior to connection to the dialysis unit, the inlet and outlet pressures, P1 and P4, at the inlet and outlet ports 20 and 21, respectively, are essentially zero. The venous pressures, P2 and P3, applied to the inlet and outlet fluid conduits 17 and 18, respectively, by the bloodstream flowing through the vein are relatively low as compared to the magnetic force generated by the internal and external magnets 30 and 29. Therefore, the spool 23 stays in its central closed position in which the inlet and outlet fluid conduits 17 and 18 are occluded by the end portions 24 and 25 of the spool, thereby preventing blood flow from the vein or air flow into the vein.

Once connected and activated, the dialysis unit simultaneously applies a positive injection fluid pressure +P1 at the inlet port 20 and a negative aspiration fluid pressure −P4 at the outlet port 21. The positive injection pressure +P1 applied at the inlet port 20 acts upon both the inlet end portion 24 and the shoulder portion 26 of the spool 23 overcoming the magnetic force applied by magnets 29 and 30 to move the spool in the direction of the applied pressure +P1 (i.e., to the right as shown in FIG. 2b) and against the magnetic force so that the inlet end portion 24 slides away from the inlet fluid conduit 17. Similarly, the negative aspiration pressure −P4 applied at the outlet port 21 simultaneously acts upon both the outlet end portion 25 and the shoulder portion 26 to move the spool 23 against the magnetic force and in the direction of the applied pressure −P4 until the outlet fluid conduit 18 is no longer blocked by the outlet end portion 25. With the end portions 24 and 25 no longer occluding the inlet and outlet fluid conduits 17 and 18, blood may flow to and from the dialysis unit through the body portion 11. Specifically, blood flows from the dialysis unit into the inlet conduit 17 past the end of the inlet end portion 24 and blood flows into the dialysis unit from the outlet conduit 18 around the neck portion 27 between the outlet end portion 25 and the shoulder portion 26 of the spool with the spool moved to the right as shown in FIG. 2b. When the dialysis procedure is completed and the unit is turned off, the inlet and outlet pressures P1 and P4 applied to the inlet and outlet ports 20 and 21 return to zero and the magnetic force of the magnets 29 and 30 returns the spool 23 to its central closed position wherein the inlet and outlet conduits 17 and 18 are again blocked as shown in FIG. 2a.

The operation described above relates specifically to a hemodialysis procedure in which the catheter is connected to a dialysis unit. However, the self-occluding catheter of the present invention may be utilized in a variety of other typical medical procedures. For example, in the process of drawing blood a syringe may be inserted in either the inlet or outlet port 20 or 21 and a negative aspiration pressure may be applied with the syringe as shown in FIG. 2c. As a result, the spool 23 moves in response to the negative fluid pressure, as described above, to unblock the respective fluid conduit so that blood may flow around the neck portion 27 of the spool. Similarly, a positive fluid pressure, such as applied when administering a medication with a syringe, may be applied alone to either port thereby moving the spool against the magnetic force to open the inlet conduit as described above. Accordingly, the self-occluding catheter of the present invention is not limited to hemodialysis procedures.

FIG. 3 shows an alternate embodiment of the present invention in which the tubular extension 14 is formed together with the body portion 11 as a unitary catheter. FIG. 3 also illustrates an alternate embodiment of the spool 31 comprising two opposite end portions 32 and 33 and a single central neck portion 34. The end portions 32 and 33 have a diameter approximately equal to but slightly less than the diameter of the transverse bore 19 such that the end portions fit in close sliding relationship within the transverse bore. The end portion 32 adjacent the inlet fluid conduit 17 also includes an annular groove for receiving a respective sealing ring 28. As an alternative to integrally molded internal magnets 30, the spool 31 of FIG. 3 is magnetically charged (i.e. positively or negatively) by impregnating the polymeric molding material of the spool with a positively or negatively charged ferrous material during molding. Thus, the entire spool 31 is positively or negatively magnetically charged. Again, depending on the magnetic charge of the spool, the oppositely disposed external magnets 29 are positioned within the transverse bore 19 such that their polarities generate a magnetic force urging the spool into a central closed position in which the end portions 32 and 33 occlude the inlet and outlet fluid conduits 17 and 18 as illustrated in FIGS. 3 and 4a.

Operation of this alternate embodiment is similar to that as described above. Referring to FIGS. 4a, 4b and 4c, when the spool 31 is in its central normally closed position, the end portions 32 and 33 of the spool completely occlude the inlet and outlet fluid conduits 17 and 18, respectively. When a positive injection pressure +P1 is applied to the inlet port 20 and/or a negative aspiration pressure −P4 is applied to the outlet port 21, the fluid pressure acts upon the spool 31 to slide it into its open position (i.e., to the right as shown in FIG. 4b). In its open position blood flows past the end of the inlet end portion 32 into the inlet conduit 17 and blood flows around the neck portion 34 of the spool 31 from the outlet conduit 18. As shown in FIG. 4c, either a positive or a negative fluid pressure applied alone will move the spool 31 to its open position. The difference here, however, is that the inlet port 20 must be dedicated to receive a positive fluid pressure and the outlet port 21 must be dedicated to receive a negative fluid pressure, whereas in the preferred embodiment, the ports are interchangeable (i.e., both ports can receive either a positive or a negative fluid pressure).

Figure 5:
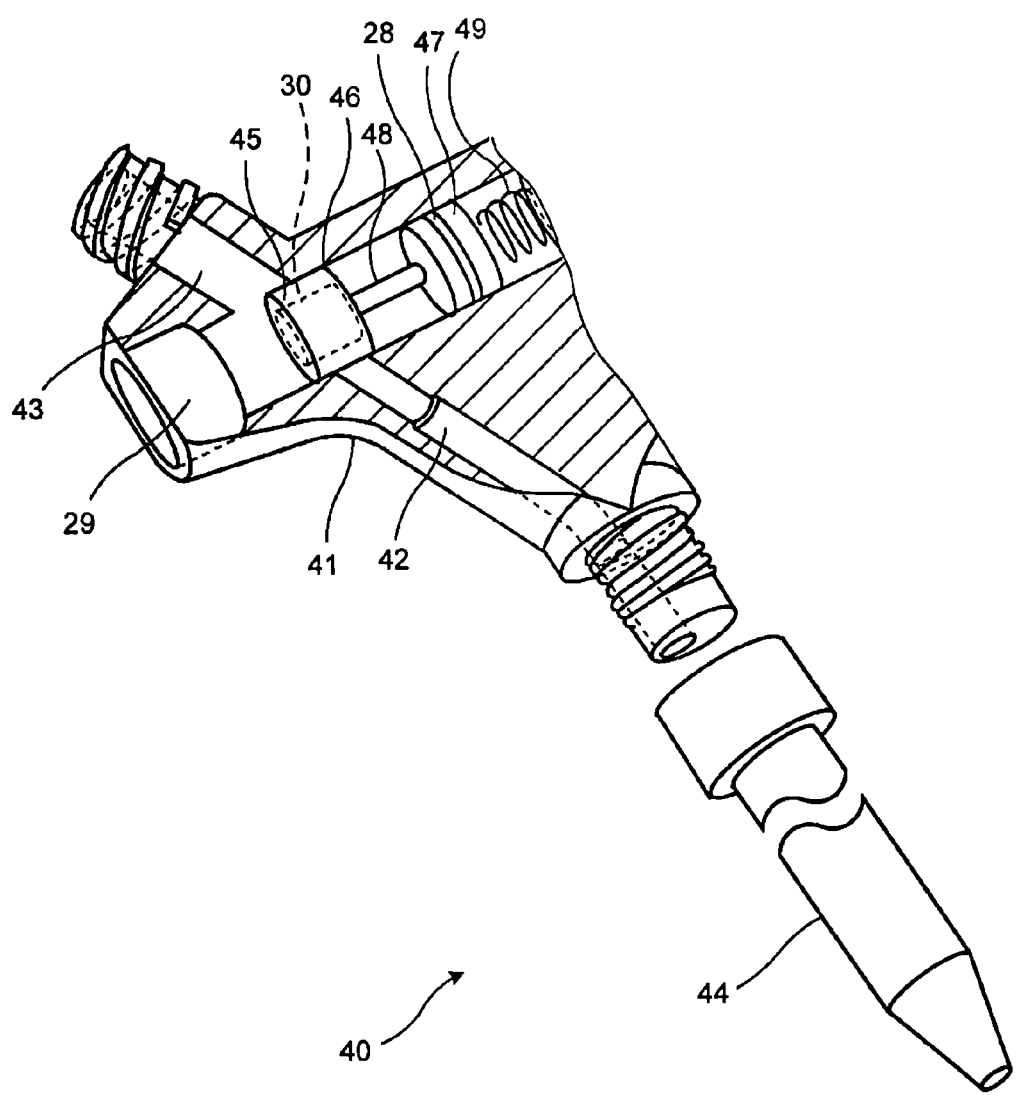
FIG. 5 is a perspective, partial cross-sectional, view of another alternate embodiment of the self-occluding catheter formed in accordance with the present invention.

FIG. 5 shows another alternate embodiment of the present invention in which a single-lumen catheter 40 and an alternate biasing device is utilized. In this embodiment, the body portion 41 includes only one internal fluid conduit 42 and port 43 which is in fluid communication with a single lumen (not shown) of the tubular portion 44. The single-lumen catheter 40 of FIG. 5 may be utilized in such typical medical procedures as drawing blood and administering medication. The single lumen catheter 40 of FIG. 5 is shown to be essentially one-half of the catheter 10 shown in FIG. 1. Other configurations of single lumen catheter 40 are within the contemplation of the present invention.

The spool 45 of FIG. 5 is similar to the spool 31 shown in FIG. 3 in that it includes two opposite end portions 46 and 47 in close sliding relationship with the transverse bore 19 and a reduced diameter central neck portion 48. In the present embodiment, however, the sealing ring 28 is fixed on the end portion 47 opposite the conduit blocking end portion 46. The spool 45 may be molded with internal magnets 30 in both end portions 46 and 47 which are magnetically urged by two external magnets 29 fixed at opposite ends of the transverse bore 19, as described above. Alternatively, a spring 49 may take the place of one or both of the external magnets 29 for urging the spool 45 to its central closed position. FIG. 5 shows a spring and magnet combination, however, a properly sized spring alone can provide the positioning and resiliency required of the spool. Any combination of springs or magnets may be utilized in any of the above embodiments of the present invention, however, the biocompatibility of these devices must be taken into consideration if either is in contact with the blood flowing through the catheter.

Figure 6A:
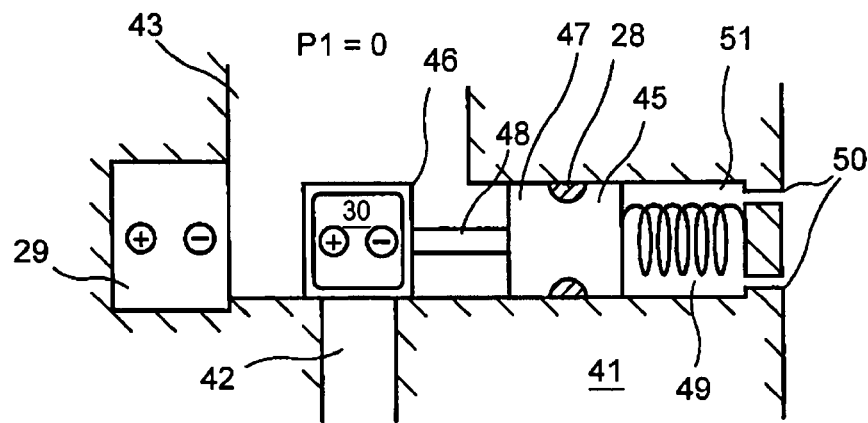
FIGS. 6a, 6b and 6c are schematic drawings illustrating the operation of the catheter shown in FIG. 5.
Figure 6B:
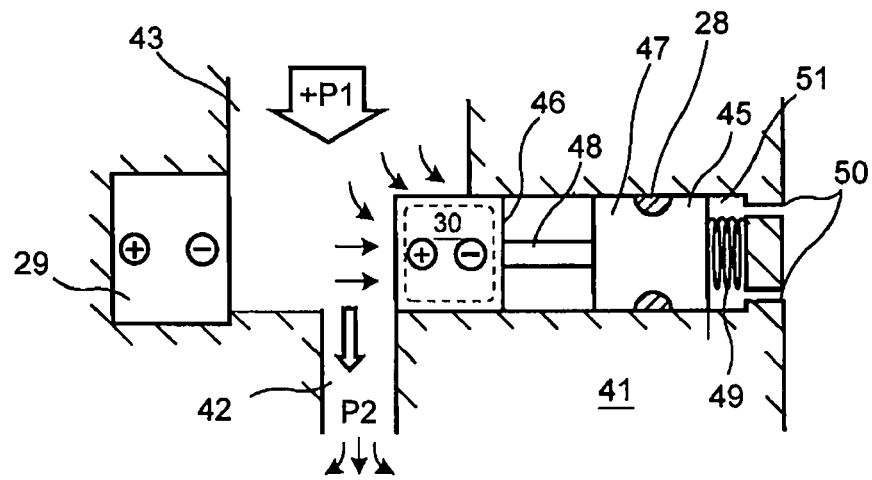
Figure 6C:
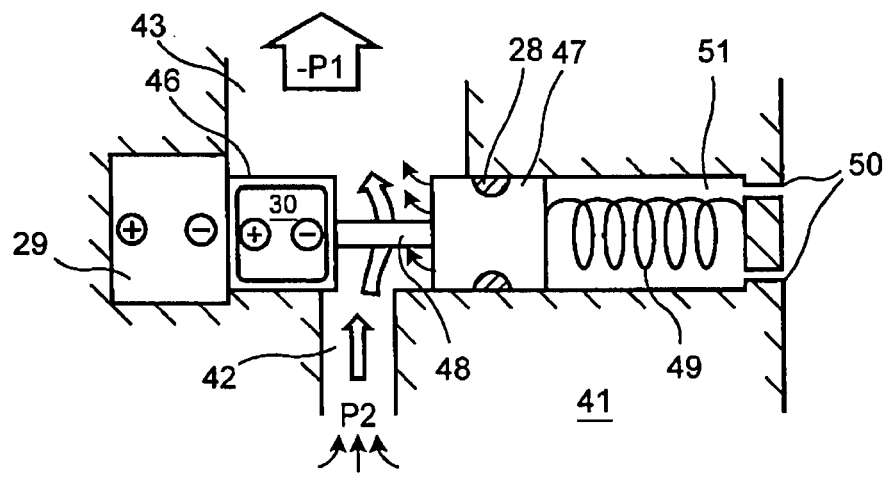

FIGS. 6a, 6b and 6c illustrate the operation of the single-lumen catheter 40. When no pressure is applied at the connection port 43 (i.e., P1=0), the magnets and/or springs urge the spool 45 to its normally closed position wherein the conduit blocking end portion 46 occludes the internal fluid conduit 42 of the body. When a positive injection pressure +P1 is applied to the connection port 43, the fluid pressure acts upon both end portions 46 and 47 urging the spool 45 to the right as shown in FIG. 6b wherein the conduit blocking end portion 46 is moved out of the way of the internal conduit 42, thereby allowing fluid flow from the proximal end to the distal end of the catheter. Vents 50 are provided through the body portion 41 to vent the volume within the chamber 51 surrounding the spring 49 so that the spool 45 may move within the transverse bore. Referring to FIG. 6c, when a negative aspiration pressure −P1 is applied to the connection port 43, the escaping fluid pressure draws both end portions 46 and 47 of the spool 45 to the left wherein the internal fluid conduit 42 is again opened and fluid may flow from the distal end of the catheter to the proximal end of the catheter around the neck portion 48 of the spool.

Any combination of the above embodiments may be utilized in the present invention without taking away from the scope of the invention. What is provided as a result is a reduced size, light-weight catheter which reduces the discomfort to the patient and requires less manipulation by the medical professional to complete a given medical procedure. Notably, there are no requirements for extension tubes or clamps at the connection ports to stop blood flow after the procedure has been conducted. The device is also tamper resistant and is less prone to inadvertent manipulation. The device may be designed to be a unitary catheter or may be a catheter connector in which any desired catheter tube may be selected and connected to the body portion.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention, and it is intended to claim all such changes and modifications as fall within the scope of the invention.

What is claimed is:

1. A self-occluding catheter comprising:
   a body portion having an inlet port having an inlet conduit extending therefrom, an outlet port having an outlet conduit extending therefrom and a transverse bore in fluid communication with said inlet conduit and said outlet conduit;
   an occluding device movably supported within said transverse bore of said body portion for movement between a closed position occluding said inlet and outlet conduits, and an open position opening said inlet and outlet conduits; and
   a biasing device for resiliently maintaining said occluding device in said closed position;
   said occluding device being movable from said closed position to said open position against said resilient bias upon pressure applied by a fluid passed between said inlet and outlet conduits.

2. A self-occluding catheter of claim 1 wherein said occluding device includes a spool slidably supported within said transverse bore.

3. The self-occluding catheter as defined in claim 2, wherein said spool is magnetically charged and said biasing device including a magnet fixed adjacent said spool, said magnet generating a magnetic force for resiliently urging said spool to said closed position.

4. The self-occluding catheter connector as defined in claim 3, wherein said spool includes an internal magnet for providing said magnetic charge.

5. The self-occluding catheter connector as defined in claim 2, wherein said biasing device comprises a spring positioned adjacent said spool for spring biasing said spool to said closed position.

6. The self-occluding catheter connector as defined in claim 2, wherein said spool comprises a cylindrical member having two opposite end portions and a central portion, said end portions having two opposite end portions and a central portion, said end portions having a diameter slightly less tnan the diameter of said transverse bore for providing a close sliding relationship between said end portions and said transverse bore, said end portions simultaneously blocking said inlet and outlet fluid conduits when said spool is in said closed position, and said central portion having a smaller diameter than said end portions for permitting flow around said spool when said spool is in said open position.

7. The self-occluding catheter connector as defined in claim 6, wherein at least one of said end portions includes a sealing ring for preventing fluid flow between said inlet and said outlet fluid conduits.

8. The self-occluding catheter of claim 1 further including:
   an elongated tubular extension attached to said distal body portion for insertion into a body cavity, said tubular extension having a pair of lumens, each said lumen in fluid communication with a respective one of said inlet and outlet conduits of said body portion.

9. The self-occluding catheter of claim 8, wherein said tubular extension is releasably connected to said body portion.

10. The self-occluding catheter of claim 8, wherein said tubular extension is integrally formed with said body portion.

* * * * *